United States Patent [19]

Furutachi et al.

[11] 4,293,691
[45] Oct. 6, 1981

[54] METHOD FOR PREPARING MAGENTA COUPLERS HAVING THIOETHER GROUPS

[75] Inventors: Nobuo Furutachi; Nobuo Seto, both of Minami-ashigara, Japan

[73] Assignee: Fuji Photo Film Co., Ltd., Minami-ashigara, Japan

[21] Appl. No.: 65,407

[22] Filed: Aug. 10, 1979

[30] Foreign Application Priority Data

Aug. 10, 1978 [JP] Japan ................................. 53-97574

[51] Int. Cl.$^3$ ................. C07D 413/12; C07D 401/12; C07D 403/12; C07D 231/48
[52] U.S. Cl. .................................... 544/140; 548/360; 548/364; 548/365; 548/324; 548/163; 548/170; 548/221; 548/222; 548/225; 548/226; 548/227; 548/228; 548/230; 548/253; 548/261; 548/309; 548/327; 548/336; 548/348; 544/371; 546/153; 546/162; 546/211; 546/279
[58] Field of Search ............... 548/360, 324, 364, 365, 548/163, 170, 221, 222, 225, 226, 227, 228, 230, 253, 261, 309, 327, 336, 348; 544/140, 371; 546/153, 162, 211, 279

[56] References Cited

U.S. PATENT DOCUMENTS

| | | | |
|---|---|---|---|
| 3,061,432 | 10/1962 | Menzel et al. | 548/360 |
| 3,227,554 | 1/1966 | Barr et al. | 430/387 |
| 3,701,783 | 10/1972 | Barr et al. | 548/251 |
| 3,928,044 | 12/1975 | Arai et al. | 548/360 |
| 3,930,861 | 1/1976 | Van Poucke et al. | 548/360 |
| 4,032,346 | 6/1977 | Furutachi et al. | 548/324 |
| 4,040,836 | 8/1977 | Arai et al. | 548/360 |

OTHER PUBLICATIONS

Sirakawa et al., Chem. Pharm. Bull., 1970, vol. 18(2), pp. 235-242.
Wiley et al., Pyrazolones, Pyrazolidones, and Derivatives, Interscience, N.Y., 1964, pp. 19 and 63.
Angelini et al., Chem. Abst., 1956, vol. 50, p. 3416.

Primary Examiner—Henry R. Jiles
Assistant Examiner—Natalia Harkaway
Attorney, Agent, or Firm—Sughrue, Mion, Zinn, Macpeak and Seas

[57] ABSTRACT

A method for preparing image-forming color couplers containing a thioether group at the coupling active position is disclosed which comprises reacting a compound of the formula A-H where A is a cyan, magenta or yellow coupler residue in which a hydrogen atom at the coupling off position is removed with a disulfide of the formula (IIa) or (IIb):

$$R-S-S-C(=N-R_1)(N-R_2 R_3) \cdot HX \quad \text{(IIa)}$$

$$R-S-S-C(=N-R_1)(N-R_2 R_3) \quad \text{(IIb)}$$

where R is a straight chain, branched chain or cyclic alkyl group, a cyclic alkenyl group, or an aralkyl group or a $$-\underset{\underset{B}{|}}{\overset{Z}{\overset{\|}{C}}}$$

group, B is Y, -D-Y or $$-N{\overset{\frown}{Q}}$$

where D is an oxygen atom or >N—R$_4$, R$_4$ is a hydrogen atom, an alkyl group or an aryl group, Y is a straight chain, branched chain or cyclic alkyl group, a straight chain, branched chain or cyclic alkenyl group, an aralkyl group, an aryl group, or a heterocyclic group, Q is a non-metallic atomic group necessary for completing a 5- or 6-membered nitrogen-containing heterocyclic group and R$_1$, R$_2$ and R$_3$ each is a hydrogen atom, an alkyl group, a cycloalkyl group, or an aryl group, an R$_2$ and R$_3$ or R$_1$ and R$_3$ can combine to form a 5-, 6- or 7-membered nitrogen-containing heterocyclic ring, and X is a halogen atom.

11 Claims, No Drawings

METHOD FOR PREPARING MAGENTA COUPLERS HAVING THIOETHER GROUPS

BACKGROUND OF THE INVENTION

1. Field of the Invention

The present invention relates to a method for preparing a color image-forming coupler which is used for color photography, and more particularly to a novel method for preparing a color image-forming coupler which contains a thioether group at the coupling active point.

2. Description of the Prior Art

In color photography using silver halide light-sensitive materials a color image-forming coupler is incorporated into a developing solution, a photographic emulsion layer, or another hydrophilic colloid layer and is reacted with the oxidation product of the color developing agent, which is formed upon development of an exposed silver halide emulsion layer, to form non-diffusible color images. Most of the conventional couplers are four-equivalent couplers which stoichiometrically require 4 mols of exposed silver halide as an oxidizing agent to form 1 mol of dye. Where a large amount of silver halide is incorporated into a light-sensitive emulsion layer, there are disadvantages. Light-scattering is increased in the emulsion layer, image sharpness is reduced, and, with the increase of the thickness of the emulsion layer, photographic processing speed is retarded. Further, since the formation of dyes from the couplers is generally not completed in the color developing solution, it is necessary to employ a strong oxidizing agent in a processing step following the color development to complete the formation of dyes.

In order to overcome these disadvantages, two-equivalent couplers have been proposed which require only 2 mols of exposed silver halide to form 1 mol of dye. A two-equivalent coupler has such a structure that a hydrogen atom at the coupling position (e.g., the p-position of phenolic hydroxyl group, the active methylene group at the 4-position of 5-pyrazolone, or the active methylene of acylacetonalide) is substituted with a group which is released upon coupling. A development inhibitor releasing coupler (a so-called DIR coupler) is a known two-equivalent coupler used to increase sharpness of color images and improve granularity of color images due to an edge effect in the layer, or to carry out color correction by an interlayer effect. A so-called BAR coupler which releases a bleach promotor is another two-equivalent coupler used for bleaching silver remaining in the emulsion layer. Of these couplers, there is a coupler which releases a mercaptan upon coupling reaction with a oxidation product of a phenylenediamine type developing agent. These two-equivalent couplers and methods for preparing them are disclosed, for example, in U.S. Pat. Nos. 3,227,554 and 3,701,783, and methods for preparing the two-equivalent couplers capable of releasing a mercaptan are disclosed in German Patent Application (OLS) No. 2,343,378 and Research Disclosure, Vol. 10, No. 138 (1975).

The present invention relates to a novel method for preparing two-equivalent yellow, magenta or cyan couplers which release a mercaptan upon coupling reaction.

The method disclosed in U.S. Pat. Nos. 3,227,554 and 3,701,783 comprises converting a mercaptan which will be released into a sulfonyl halide and reacting it with a four-equivalent coupler having no substituent at the coupling active position to introduce a thioether group into the coupler. This method can be applied to arylmercaptans and heterocyclic mercaptans, but if it is applied to alkylmercaptans the yield of the final product is markedly reduced due to the production of by-products. The method disclosed in U.S. Pat. No. 4,032,346 has such disadvantages that the synthesis of symmetrical disulfide compounds is difficult and the method cannot be effectively applied to the preparation of alkylmercaptans. The symmetrical disulfides disclosed in the '346 Patent are electron attractive as shown by the formulae:

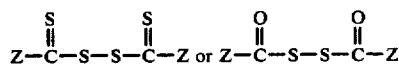

wherein Z is a substituent such as tetraalkyl thiuramdisulfide or di(alkoxythiocarbonyl)disulfide. A final product can be prepared in a high yield by reacting 1,3-di-substituted-5-oxo-2-pyrazoline with the sulfide. However, half of the mercaptan compound in the disulfides is not effectively used. Even if this method is applied to alkylmercaptans to synthesize a dialkyldisulfide which is then reacted with 1,3-di-substituted-5-oxo-2-pyrazoline in the presence of a base, the final product, 1,3-di-substituted-4-alkylthio-5-oxo-2-pyrazoline cannot be synthesized as will later be shown by Comparative Example 2. Thus, the method is not useful for the synthesis of 4-alkylthio-5-oxo-2-pyrazoline.

According to the method disclosed in German patent application (OLS) No. 2,343,378, a dihalide that is a pyrazolone coupler having two halogen atoms in the coupling active position thereof is used as a starting material and is reacted with not less than 2 mols of mercapto compound to introduce a thioether group at the 4-position of the pyrazolone. The disadvantages of this method are the dihalide is unstable to heat, the by-products increase, and the reaction does not proceed effectively.

The method disclosed in Research Disclosure, Vol. 10, No. 138 comprises dropwise adding a bromine in the presence of a four-equivalent coupler of which the coupling active position is unsubstituted, and a heterocyclic mercapto compound to introduce a mercapto group into the coupling active position. Mercapto compounds which are effectively applied to the method are limited. For example, the method is useful for the synthesis of a heterocyclic mercaptan and an arylmercaptan, but is not useful for an alkylmercaptan due to the increased by-products.

As will be explained below the method of the present invention can be widely used because it has advantages, for example, a thioether group can be introduced directly into a coupling active position of a yellow, magenta or cyan coupler.

SUMMARY OF THE INVENTION

A first object of this invention is to provide a novel method by which a thioether group is introduced into a coupling active position of a coupler.

A second object of this invention is to provide a method for introducing a thioether group with high yield by simple operations.

A third object of this invention is to provide a novel method of preparing a compound having a substituent capable of being released upon oxidation coupling with a p-phenylenediamine color developing agent at the coupling active position of couplers.

A fourth object of this invention is to provide a practical method of preparing various couplers having a thioether group.

A fifth object of this invention is to provide a thioether releasing type coupler in high purity.

A sixth object of this invention is to provide a mercaptan-releasing coupler having excellent photographic properties.

The above objects of this invention are attained by the direct reaction of a coupler in which the coupling active position is unsubstituted with a disulfide represented by the formula (IIa) or (IIb) to prepare a two-equivalent coupler represented by the formula (I). That is, a compound of the formula A-S-R is prepared from a coupler, A-H in which the coupling active position is unsubstituted.

DETAILED DESCRIPTION OF THE INVENTION

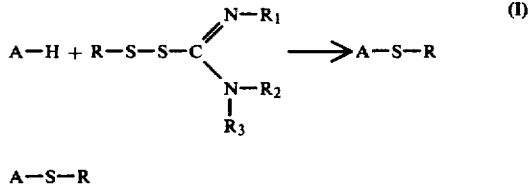

(I)

A—S—R

In the formula (I) A is a yellow coupler, a magenta coupler or a cyan coupler residue in which a hydrogen atom at the coupling active position is eliminated, R is a straight chain, branched chain or cyclic alkyl group, a cyclic alkenyl group, or an aralkyl group, or a

group, B is Y, -D-Y or

where D is an oxygen atom or $>N-R_4$, $R_4$ is a hydrogen atom, an alkyl group or an aryl group, Y is a straight chain, branched chain or cyclic alkyl group, a straight chain, branched chain or cyclic alkenyl group, an aralkyl group, an aryl group, or a heterocyclic group, Q is a non-metallic atomic group necessary to complete a 5- or 6-membered nitrogen-containing heterocyclic group.

R may be a straight or branched chain alkyl group having 1 to 22 carbon atoms such as a methyl group, an ethyl group, an isopropyl group, an n-butyl group, a tert-butyl group, a hexyl or heptadecyl group. R may also be an alkenyl group having 1 to 22 carbon atoms such as an allyl group and an oleyl group, a cyclic alkyl group having 5 to 22 carbon atoms such as a cyclohexyl group, a cyclohexylmethyl group, a cyclic alkenyl group such as a cyclohexenyl group and a mono or bicyclic aralkyl group having 6 to 22 carbon atoms such as a benzyl group, a p-nitrobenzyl group, and a β-phenylethyl group. These R groups may be substituted in a manner known in the art. For example, these groups may be substituted by a halogen atom, a nitro group, a cyano group, an alkoxy group, an aryloxy group, a carboxy group, an alkylcarbonyl group, an alkylthiocarbonyl group, an arylcarbonyl group, an arylthiocarbonyl group, an alkoxycarbonyl group, an aryloxycarbonyl group, a sulfo group, an acyloxy group, a sulfamoyl group, a carbamoyl group, a thiocarbamoyl group, an acylamino group, a diacylamino group, a ureido group, a thioureido group, a urethane group, a thiourethane group, a sulfonamido group, a heterocyclic ring, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-arylanilino group, an N-alkylanilino group, an N-acylanilino group, a hydroxy group or a mercapto group wherein the number of carbon atoms for the alkyl group is preferably 1 to 22. In this and the following description unless otherwise indicated, the carbon atom range for substituents of an aliphatic nature such as an alkyl group, an alkenyl group, a cycloalkyl group, an aliphatic acyl group, an aralkyl group, etc., is 1 to 22 including their substituents (in total) and 6 to 32 for groups of aromatic nature such as aryl, aromatic acyl, aromatic heterocyclic, etc., including their substituents.

Y may be a straight chain, branched chain or cyclic alkyl group, a straight chain, branched chain or cyclic alkenyl group, an aralkyl group, an aryl group, or a heterocyclic group each of which may contain up to 40 carbon atoms. More specifically, Y may be a straight or branched chain alkyl group having 1 to 22 carbon atoms (e.g., a methyl, ethyl, isopropyl, butyl, isobutyl, dodecyl, stearyl group), an alkenyl group having 1 to 22 carbon atoms (e.g., an allyl or oleyl group), a cyclic alkyl group having 5 to 22 carbon atoms (e.g., a cyclopentyl or cyclohexyl group), a mono or bicyclic aralkyl group having 6 to 32 carbon atoms (e.g., a benzyl or β-phenylethyl group) and a cyclic alkenyl group having 5 to 22 carbon atoms (e.g., a cyclopentenyl or cyclohexenyl group). These groups can be substituted with a halogen atom, a nitro group, a cyano group, an aryl group, an alkoxy group, an aryloxy group, a carboxy group, an alkylcarbonyl group, an alkoxycarbonyl group, an aryloxycarbonyl group, a sulfo group, a sulfamoyl group, a carbamoyl group, an acylamino group, a diacylamino group, a ureido group, a thioureido group, a sulfonamido group, a urethane group, a heterocyclic group (e.g., pyridyl, quinolyl, furyl or piperidyl), an arylsulfonyl, an alkylsulfonyl, an arylsulfonyloxy, an alkylsulfonyloxy, an arylthio, an alkylthio, an alkylsulfinyl, an arylsulfinyl or a substituted amino group (e.g., an N,N-diethylamino group).

The aryl group for Y may have 6 to 32 carbon atoms and includes polycyclic aryl groups, e.g., a phenyl group, an α- or β-naphthyl group, a substituted phenyl group, a substituted naphthyl group, etc., which can be substituted with one or more of an alkyl group, an aralkyl group, an alkenyl group, a cyclic alkyl group, a cyclic alkenyl group, a halogen atom, a nitro group, a cyano group, an aryl group, an alkoxy group, an aryloxy group, a carboxy group, an alkylcarbonyl group, an arylcarbonyl group, an alkoxycarbonyl group, an aryloxycarbonyl group, a sulfo group, an acyloxysulfamoyl group, an N,N-dialkylsulfamoyl group, an N-alkyl-N-arylsulfamoyl group, an N-alkylsulfamoyl group, an N-arylsulfamoyl group, a carbamoyl group, an N-alkylcarbamoyl group, an N,N-dialkylcarbamoyl group, an N-alkyl-N-arylcarbamoyl group, an N-arylcarbamoyl group, an acylamino group, a diacylaminoureido group, a thioureidosulfonamido group, a urethane group, a thiourethane group, a heterocyclic ring (e.g., pyridyl, quinolyl, furyl or piperidyl), an alkylsulfonyl group, an arylsulfonyl group, an alkylthio group, an arylthio group, an alkylsulfinyl group, an arylsulfinyl group or a substituted amino group (e.g., an N,N-dialkylamino group, an anilino group, an N-acylanilino group or an N-arylanilino group).

A heterocyclic group for Y includes 5- to 7-membered nitrogen-containing heterocyclic groups (e.g., pyridyl, quinolyl, pyrrolidyl, a heterocyclic group having two or more nitrogen atoms such as benzimidazolyl, etc., which can be substituted with the substituent for the above-described aryl group), oxygen-containing heterocyclic groups (e.g., tetrahydrofurfuryl, benzofuryl, etc., which can be substituted with the substituent for the above-described aryl group), sulfur-containing heterocyclic groups (e.g., thienyl, benzothienyl, etc., which can be substituted with the substituent for the above-described aryl group) or a heterocyclic groups having two or more different hetero atoms (e.g., benzoxazolyl, benzothiazolyl, etc.).

Y is preferably an alkyl group or an aryl group as described above.

$R_4$ is an alkyl group, an aryl group or a hydrogen atom, as defined above for R.

Q represents the non-metallic atoms necessary to complete a 5- or 6-membered heterocyclic ring. Q may contain hetero atom in addition to the nitrogen atom such as an oxygen, sulfur or nitrogen atom. Suitable heterocyclic groups include pyrrolidine, piperidine, morpholine, imidazole, benzimidazole, phthalimide, succinimide, glutarimide, hydantoin, oxazolidindion, benzotriazole, α-pyridone, γ-pyridone, oxazolidone, valerolactam, butyrolactam, thiohydantoin, naphthotriazole, tetrazole, pyrazole, indole, imidazoline, pyrazoline, piperazine, indoline and isoindoline.

The residue represented by A of a yellow color image-forming couplers may be a pivalylacetanilide coupler nucleus, a benzoylacetanilide coupler nucleus, a malondiamide coupler nucleus, a benzothiazolyl coupler nucleus, a benzoxazolylacetamide coupler nucleus, a benzoxazolylacetate coupler nucleus, a benzimidazolylacetamide coupler nucleus, a benzimidazolylacetate coupler nucleus, and a residue derived from an acetamide or acetate substituted with a heterocyclic group as disclosed in U.S. Pat. No. 3,841,880 is preferred.

The residue represented by A of a magenta color image-forming couplers may be a 5-oxo-2-pyrazoline coupler nucleus and a pyrazolo[1,5-a]benzimidazole coupler nucleus is preferred.

The residue for cyan color image-forming couplers represented by A may be a phenol coupler nucleus or an α-naphthol coupler nucleus.

More specifically the residues represented by A and useful in this invention are represented by the following formulae (III), (IV), (V), (VI), (VII) or (VIII).

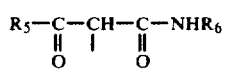
(III)

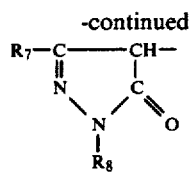
(IV)

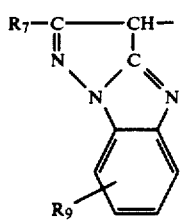
(V)

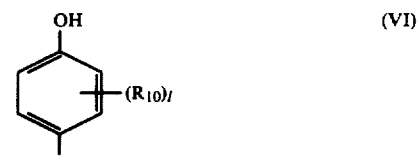
(VI)

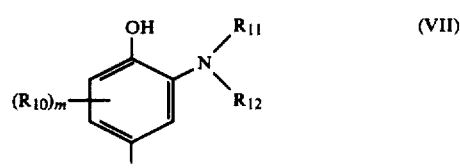
(VII)

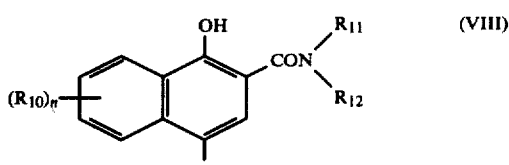
(VIII)

In the above formulae $R_5$ is an aliphatic group, an aromatic group or a heterocyclic group, and $R_6$ is an aromatic group or a heterocyclic group.

The aliphatic group for $R_5$ preferably has 1 to 22 carbon atoms and may be substituted or unsubstituted and straight chain, branched chain or cyclic. The preferred substituents for the alkyl group are an alkoxy group, an aryloxy group, an amino group and an acylamino group which can be substituted. As the typical examples of the aliphatic group for $R_5$, there are an isopropyl group, an isobutyl group, a tert-butyl group, an isoamyl group, a tert-amyl group, a 1,1-dimethylbutyl group, a 1,1-dimethylhexyl group, a dodecyl group, a hexadecyl group, an octadecyl group, a cyclohexyl group, a 2-methoxyisopropyl group, a 2-phenoxyisopropyl group, a 2-p-tert-butylphenoxyisopropyl group, an α-aminoisopropyl group, an α-(diethylamino)isopropyl group, an α-(succinimido)isopropyl group, an α-(phthalimido)isopropyl group, an α-(benzenesulfonamido)isopropyl group, etc. Again, in the following description unless otherwise indicated, the carbon atom range for substituents of an aliphatic nature such as an alkyl group, an alkenyl group, a cycloalkyl group, an aliphatic acyl group, an aralkyl group, etc., is 1 to 22 including their substituents (in total) and 6 to 32 for groups of aromatic nature such as aryl, aromatic acyl, aromatic heterocyclic, etc., including their substituents.

$R_5$ and $R_6$ may be an aromatic group and particularly a phenyl group or a phenyl group fused with a carbocyclic or heterocyclic 5-membered or 6-membered ring. The aromatic group preferably has 6 to 32 carbon atoms and can be substituted, for example, with an alkyl group, an alkenyl group, an alkoxy group, an alkoxycarbonyl group, an alkoxycarbonylamino group, an aliphatic amido group, an alkylsulfamoyl group, an alkylsulfonamido group, an alkylureido group, an alkylsubstituted succinimido group, etc. The alkyl may be interrupted by a divalent aromatic group such as a phenylene group. The phenyl group can be substituted with an aryloxy group, an aryloxycarbonyl group, an arylcarbamoyl group, an arylamido group, an arylsulfamoyl group, an arylsulfonamido group or an arylureido group, of which aryl group may be further substituted with an alkyl group having a total carbon atom of 1 to 22. Phenyl groups for $R_5$ and $R_6$ may be substituted with an amino group, a hydroxy group, a carboxy group, a sulfo group, a nitro group, a cyano group, a thiocyano group or a halogen atom, which may be further substituted with a lower alkyl group having 1 to 6 carbon atoms.

$R_5$ and $R_6$ may be a phenyl group fused with another alicyclic ring to form, for example, a naphthyl group, a quinolyl group, an isoquinolyl group, a chromanyl group, a cumaranyl group or a tetrahydronaphthyl group which may be further substituted.

$R_5$ and $R_6$ may be a 5- or 6-membered heterocyclic group containing at least one hetero atom selected from O, S, and N. The heterocyclic group is connected through a carbon atom thereof to the carbon atom of the carbonyl group or the nitrogen atom of the amido group in the α-acylacetamido. As the examples of the heterocyclic groups, there are thiophene, furan, pyran, pyrrole, pyrazole, pyridine, pyrazine, pyrimidine, pyridazine, indolizine, imidazole, thiazole, oxazole, triazine, oxazine, etc., which may be further substituted.

$R_8$ in the formula (IV) is a straight or branched chain alkyl group having 1 to 40 carbon atoms, preferably 1 to 22 carbon atoms (e.g., methyl, isopropyl, tert-butyl, hexyl or dodecyl), a straight or branched chain alkenyl group (e.g., allyl), a cyclic alkyl group (e.g., cyclopentyl, cyclohexyl or norbornyl), mono or bicyclic aralkyl group (e.g., benzyl or β-phenylethyl) or an alkenyl group (e.g., cyclopentenyl or cyclohexenyl), which may be substituted with a halogen atom, a nitro group, a cyano group, an aryl group, an alkoxy group, an aryloxy group, a carboxy group, an alkylthiocarbonyl group, an arylthiocarbonyl group, an alkoxycarbonyl group, an aryloxycarbonyl group, a sulfo group, a sulfamoyl group, a carbamoyl group, an acylamino group, a diacylamino group, a ureido group, a urethane group, a thiourethane group, a sulfonamido group, a heterocyclic group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxyl group or a mercapto group.

$R_8$ may be a mono or bicyclic aryl group having 6 to 32 carbon atoms (e.g., a phenyl group, an α- or β-naphthyl group). The aryl group can have one or more substituents such as an alkyl group, an alkenyl group, a cyclic alkyl group, an aralkyl group, a cyclic alkenyl group, a halogen atom, a nitro group, a cyano group, an aryl group, an alkoxy group, an aryloxy group, a carboxy group, an alkoxycarbonyl group, an aryloxycarbonyl group, a carboxy group, an alkoxycarbonyl group, an aryloxycarbonyl group, a sulfo group, a sulfamoyl group, a carbamoyl group, an acylamino group, a diacylamino group, a ureido group, a urethane group, a sulfonamido group, a heterocyclic ring, an arylsulfonyl group, an alkylsulfonyl group, an arylthio group, an alkylthio group, an alkylamino group, a dialkylamino group, an anilino group, an N-alkylanilino group, an N-arylanilino group, an N-acylanilino group, a hydroxy group or a mercapto group. The preferred example of $R_8$ is a phenyl group having an alkyl group, an alkoxy group or a halogen atom in at least one of the o-position thereof, which is useful because couplers remaining in the layer of photographic materials are not colored by light or heat.

$R_8$ may be a heterocyclic group (e.g., a 5- or 6-membered heterocyclic ring having a nitrogen atom, an oxygen atom or a sulfur atom as a heterocyclic atom, or a condensed heterocyclic ring such as a pyridyl group, a quinolyl group, a furyl group, a benzothiazoyl group, an oxazolyl group, an imidazolyl group or a napthoxazoyl group), a heterocyclic group substituted with a substituent as described above for the aryl group $R_8$, an aliphatic or aromatic acyl group, an alkylsulfonyl group, an arylsulfonyl group, an alkylcarbamoyl group, an arylcarbamoyl group, an alkylthiocarbamoyl group or an arylthiocarbamoyl group wherein the total number of carbon atoms is 3 to 32.

$R_7$ is a hydrogen atom, a straight or branched chain alkyl group having 1 to 40 carbon atoms, preferably 1 to 22 carbon atoms, a straight or branched chain alkenyl group, a cyclic alkyl group, an aralkyl group, a cyclic alkenyl group (these groups may have substituents as described for $R_8$), a mono or bicyclic aryl group, a heterocyclic group (these may have substituents as described for $R_8$), an alkoxycarbonyl group (e.g., methoxycarbonyl, ethoxycarbonyl or stearyloxycarbonyl), an aryloxycarbonyl group (e.g., phenoxycarbonyl or naphthoxycarbonyl), an aralkyloxycarbonyl group (e.g., benzyloxycarbonyl), an alkoxy group (e.g., methoxy, ethoxy or heptadecyloxy), an aryloxy group (e.g., phenoxy or tolyloxy), an alkylthio group (e.g., ethylthio or dodecylthio), an arylthio group (e.g., phenylthio or α-naphthylthio), a carboxy group, an acylamino group (e.g., acetylamino or 3-[(2,4-di-tert-amylphenoxy)acetamido]benzamido), a diacylamino group, an N-alkylacylamino group (e.g., N-methylpropionamido), an N-arylacylamino group (e.g., N-phenylacetamido), a ureido group (e.g., ureido, N-arylureido or N-alkylureido), a urethane group, a thiourethane group, an arylamino group (e.g., phenylamino, N-methylanilino, diphenylamino, N-acetylanilino or 2-chloro-5-tetradecanamidoanilino), an alkylamino group (e.g., n-butylamino, methylamino or cyclohexylamino), a 5- or 6-membered cycloamino group (e.g., piperidino or pyrrolidino), a 5- or 6-membered heterocyclic amino group containing an O, S or N atom (e.g., 4-pyridylamino or 2-benzoxazolylamino), an alkylcarbonyl group (e.g., methylcarbonyl), an arylcarbonyl (e.g., phenylcarbonyl), a sulfonamido group (e.g., alkylsulfonamido or arylsulfonamido), a carbamoyl group (e.g., ethylcarbamoyl, dimethylcarbamoyl, N-methylphenylcarbamoyl or N-phenylcarbamoyl), a sulfamoyl group (e.g., N-alkylsulfamoyl, N,N-dialkylsulfamoyl, N-alkyl-N-arylsulfamoyl or N,N-diarylsulfamoyl), a cyano group, a hydroxy group, a mercapto group, a halogen atom or a sulfo group.

$R_9$ is a hydrogen atom, a straight or branched chain alkyl group having 1 to 32 carbon atoms, preferably 1 to 22 carbon atoms, a straight or branched chain alkenyl group, a cyclic alkyl group, an aralkyl group or a cyclic alkenyl group, which may be substituted as in the case of $R_8$. Further, $R_9$ may be a mono or bicyclic aryl group or a 5- or 6-membered heterocyclic group, which may be substituted as in the case of $R_8$. $R_9$ may also be a cyano group, an alkoxy group, an aryloxy group, a halogen atom, a carboxy group, an alkoxycarbonyl group, an aryloxycarbonyl group, an acyloxy group, a sulfo group, a sulfamoyl group, a carbamoyl group, an acylamino group, a diacylamino group, a ureido group, a urethane group, a sulfonamido group, an arylsulfonyl group, an alkylsulfonyl group, an arylthio group, an alkylthio group, an alkylamino group, a dialkylamino group, an anilino group, an N-arylanilino group, an N-alkylanilino group, an N-acylanilino group, a hydroxy group or a mercapto group.

$R_{10}$, $R_{11}$ and $R_{12}$ each is a conventional four-equivalent phenol or α-naphthol coupler substituent. That is, $R_{10}$ is a hydrogen atom, a halogen atom, an aliphatic hydrocarbon residue having 1 to 36 carbon atoms, an acylamino group, —O—$R_{13}$ or —S—$R_{13}$ ($R_{13}$ is an aliphatic hydrocarbon residye). Where at least two $R_{10}$ are present in a molecule, they can be different and the aliphatic hydrocarbon residue may be substituted.

$R_{11}$ and $R_{12}$ each is an aliphatic hydrocarbon residue, a mono or bicyclic aryl group or a 5- or 6-membered heterocyclic residue containing at least one of an O, S, or N atom, each of which may be a hydrogen atom and may be substituted. $R_{11}$ and $R_{12}$ can form a nitrogen-containing heterocyclic nucleus with each other. l is an integer of 1 to 4, m is an integer of 1 to 3 and n is an integer of 1 to 5. The aliphatic hydrocarbon residue may be saturated or unsaturated, and may be a straight, branched or cyclic structure. The preferred examples of the aliphatic hydrocarbon residue are an alkyl group (e.g., methyl, ethyl, propyl, isopropyl, butyl, tert-butyl, isobutyl, dodecyl, octadecyl, cyclobutyl or cyclohexyl), and an alkenyl group (e.g., allyl or octenyl). As examples of aryl group, there are a phenyl group and a naphthyl group. As the examples of heterocyclic residue, there are a pyridinyl group, a quinolyl group, a thienyl group, a piperidyl group and an imidazolyl group. The aliphatic hydrocarbon residue, aryl group and heterocyclic group can be substituted with a halogen atom, a nitro group, a hydroxy group, a carboxy group, an amino group, a substituted amino group, a sulfo group, an alkyl group, an alkenyl group, an aryl group, a heterocyclic group, an alkoxy group, an aryloxy group, an arylthio group, an arylazo group, an acylamino group, a carbamoyl group, an ester group, an acyl group, an acyloxy group, a sulfonamido group, a sulfamoyl group, a sulfonyl group and a morpholino group.

In this invention better results can be obtained where A is of the formulae (IV) or (V). The compounds where A is of the formula (IV) are particularly preferred because of very rapid reaction rate in the reaction of the final product having such A moiety with developing agents. Most preferably $R_7$ is an anilino group, an acylamino group or a ureido group; and $R_8$ represents a group of the formula:

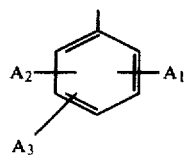

wherein $A_1$, $A_2$ and $A_3$, which may be the same or different, each represents a hydrogen atom, an alkyl group, a halogen atom, an alkoxy group, an aryloxy group, an acylamino group, a carbamoyl group, a sulfamoyl group, a sulfonyl group or a cyano group.

In more detail, $R_7$ represents anilino groups (e.g., phenylamino, o-chlorophenylamino, 2,4-dichlorophenylamino, 2,4-dichloro-5-methoxyphenylamino, 2-chloro-5-tetradecanamidophenylamino, 2-chloro-5-[α-(2,4-di-t-amylphenoxy)butyramido]phenylamino, 2-chloro-5-[(3-octadecenyl)succinimido]phenylamino, 2-chloro-5-{α-[(3-t-butyl-4-hydroxy)phenoxy]tetradecanamido}phenylamino, etc.), acylamino groups (e.g., acetylamino, butyramido, α-(3-pentadecylphenoxy)butyramido, n-tetradecanamido, α-(2,4-di-t-amylphenoxy)butyramido, 3-[α-(2,4-di-t-amylphenoxy)butyramido]benzamido, benzamido, 3-acetylamidobenzamido, etc.), ureido groups (e.g., phenylureido, methylureido, 3-[α-(2,4-di-t-amylphenoxy)butyramido]-phenylureido, etc.); $A_1$, $A_2$ and $A_3$ each represents a hydrogen atom, an alkyl group (e.g., methyl, ethyl, etc.), a halogen atom (Cl, Br, F), an alkoxy group (methoxy, ethoxy, etc.), an aryloxy group (e.g., phenyloxy, naphthyloxy, etc.), an acylamino group (e.g., acetylamino, α-(2,4-di-t-amylphenoxy)butyramido, etc.), a carbamoyl group (e.g., methylcarbamoyl, phenylcarbamoyl, etc.), a sulfamoyl group (e.g., methylsulfamoyl, phenylsulfamoyl, etc.), a sulfonyl group (e.g., ethylsulfonyl, butylsulfonyl, methylsulfonyl, etc.), or a cyano group.

In the formulae (IIa) and (IIb):

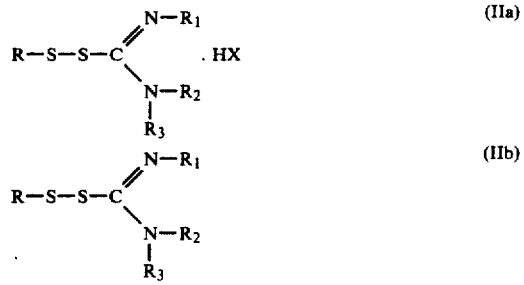

R has the same definition as in the formula (I) and X is a halogen atom (e.g., chlorine, bromine or iodine).

$R_1$, $R_2$ and $R_3$ each is a hydrogen atom, a straight or branched chain alkyl group having 1 to 22 carbon atoms (e.g., methyl, ethyl, n-butyl, tert-hexyl, n-dodecyl or n-hexadecyl) including a substituted alkyl group (substituents include halogen, cyano, methoxy, ethoxy, phenoxy, acetylamino, benzamido, ethanesulfonamido, benzenesulfonamido, N,N-diethylsulfamoyl, N,N-dimethylcarbamoyl, ethylsulfonyl, dodecylthio, nitro, hydroxy, sulfo, carboxy, benzyl, phenethyl, allyl, octadecenylsuccinimido or phthalimido), a cycloalkyl group (e.g., cyclopentyl, cyclohexyl, cycloheptyl, or cyclohexenyl), a mono or bicyclic aralkyl group (e.g., benzyl or phenethyl) or a substituted or unsubstituted phenyl group (substituents include halogen, cyano, nitro, the above-described alkyl groups, the above-described substituted alkyl groups, a phenoxy group, a phenyl group, a benzamido group, a carbamoyl group, a sulfamoyl group, an ethanesulfonamido group, an ethoxycarbonyl group, a benzyloxycarbonyl group, an acetyl group, a pivaloyl group, an ethylthio group, a phenylthio group, a phenylsulfonyl group, a hydroxy group, a carboxy group or a sulfo group). $R_1$ and $R_3$ or $R_2$ and $R_3$ may combine to from a 5-, 6- or 7-membered ring (e.g., imidazolyl, pyrrolyl, piperidyl, morpholyl ring). These rings may be substituted as described for the alkyl group for $R_1$ to $R_3$.
The typical examples of the compounds represented by the formulae (IIa) or (IIb) are shown below:
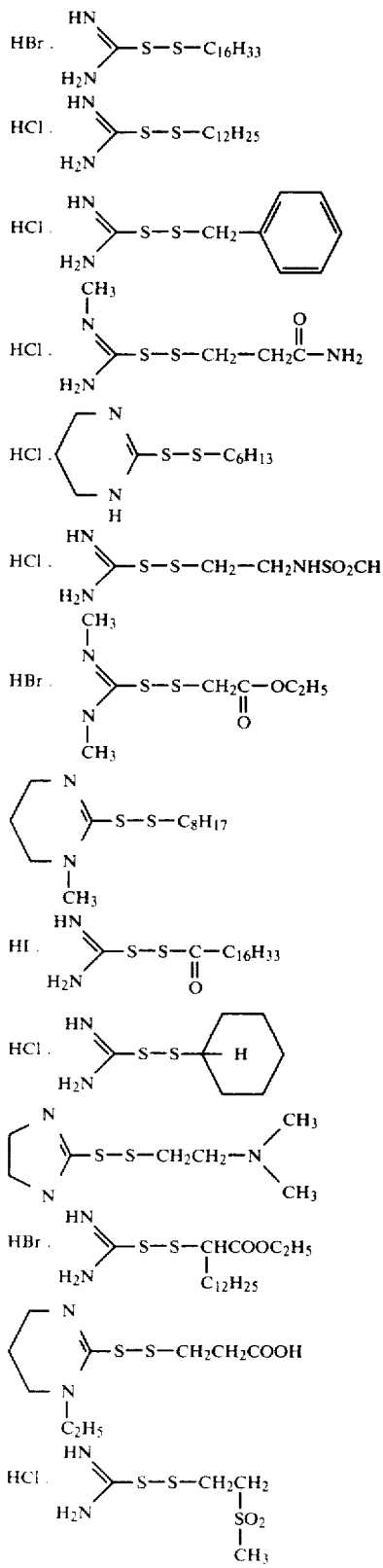
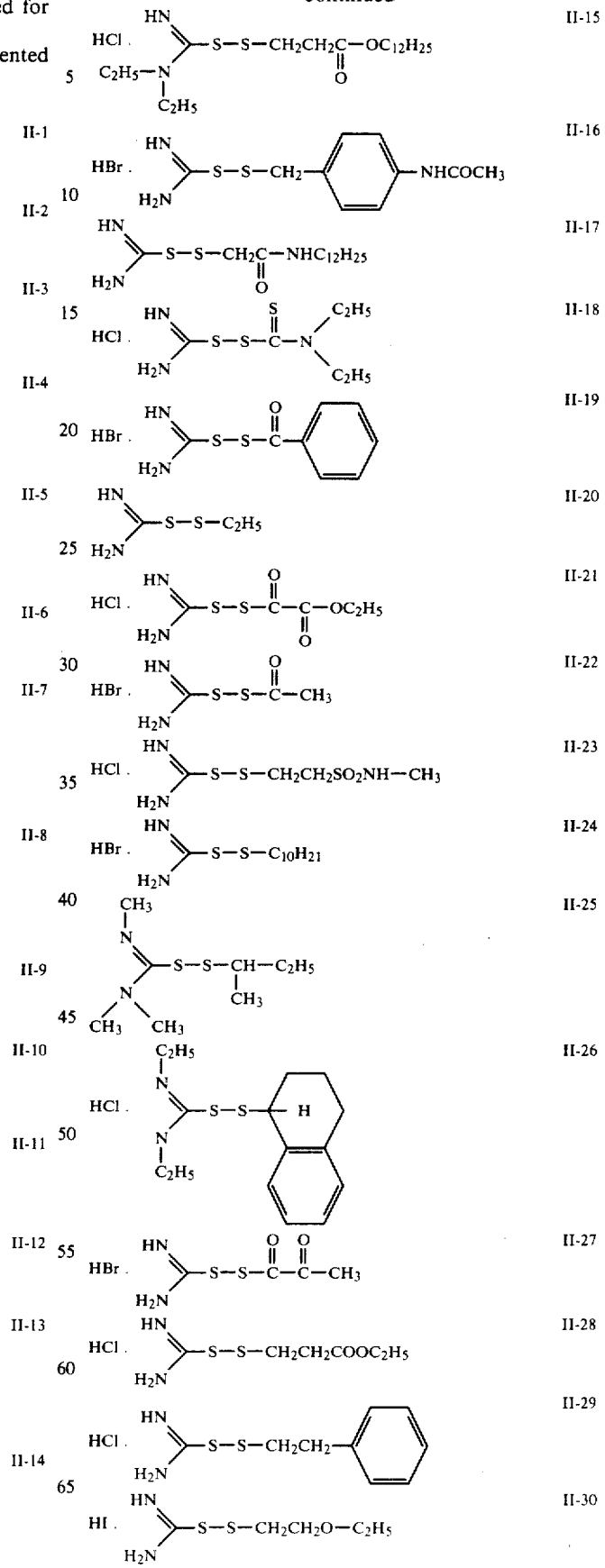

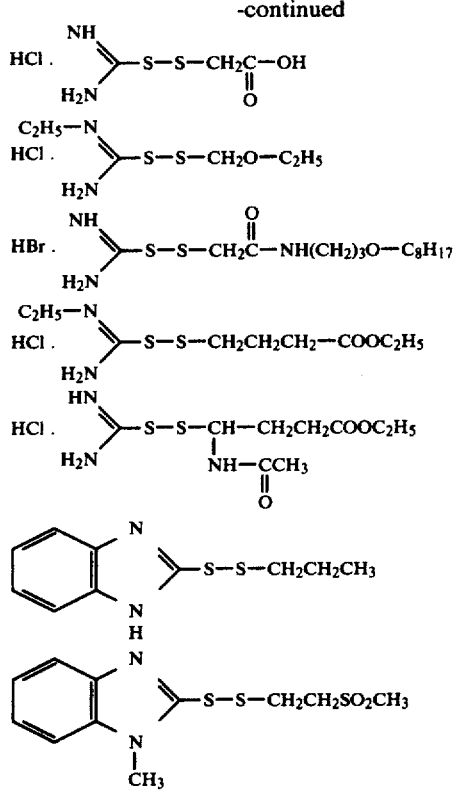

The compounds represented by the formulae (IIa) or (IIb) can be synthesized by the method disclosed in *Chem. Pharm. Bull.*, Vol. 18, pp. 235-242 (1970). That is, unsymmetrical disulfides can be synthesized by oxidizing a mercaptan and a thiourea compound with hydrogen peroxide.

In more detail, compounds of the formula (IIa) are obtained by oxidizing a mercaptan of the formula R—SH (1 mol) and a thiourea compound of the formula

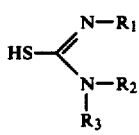

(1 mol, preferably 1.2 mol) (wherein R, $R_1$, $R_2$ and $R_3$ are the same as defined above) with 1 to 5 mols and preferably 1 to 2 mols hydrogen peroxide at about −10° to 50° C., preferably −10° to 10° C., for 1 to 10 hours under atmospheric pressure, in the presence of an aprotic solvent (e.g., ethanol, etc.) or a protic solvent (e.g., dimethylformamide, etc.). In order to obtain the compounds of the formula (IIb) the so-obtained compounds of the formula (IIa) are neutralized with a base such as triethylamine or sodium hydroxide.

SYNTHESIS EXAMPLE

Synthesis of Compound II-2

A mixture of 202 g (1.0 mol) of dodecylmercaptan, 91.2 g (1.2 mol) of thiourea, 185 ml (1.9 mol) of concentrated hydrochloric acid, 185 ml of water and 2000 ml of ethanol is stirred at 0° to 5° C. 112 g (1.45 mol) of a 35% hydrogen peroxide aqueous solution is dropwise added to the mixture over 1 hour. The resulting mixture is stirred for a further 2 hours while maintaining the system at 0° to 5° C. to induce crystallization. The crystals are removed by filtration. After thoroughly washing with water and then drying, the crystals are recrystallized from a benzene (800 ml)-n-hexane (2000 ml) solvent mixture to obtain 278 g (yield 89%) of compound II-2 having a melting point of 100° to 102° C.

In a manner similar to the above, compounds II-1, II-3 and II-38 were also synthesized in high yield.

A reaction of unsymmetrical disulfides represented by the formulae (IIa) or (IIb) with four-equivalent couplers will be explained below in detail.

A suitable molar ratio of the disulfides to the four-equivalent couplers is 1:1 to 20:1, preferably 1:1 to 2:1. Suitable reaction solvents include alcohols (e.g., methanol, ethanol or isopropanol), organic acid (e.g., acetic acid or propionic acid), halogenated hydrocarbons (e.g., chloroform or ethylene chloride), aromatic hydrocarbons (e.g., benzene, toluene or xylene), esters (e.g., ethyl acetate), non-proton type polar solvents (e.g., dimethylformamide, dimethyl sulfoxide or hexamethylphosphotriamide), water and acetonitrile. Particularly, alcohols and mixtures of alcohols and water are preferable solvents. A suitable coupler concentration is solvent to coupler volume to weight ratio of 0.5 to 20 and preferably 1 to 10.

The reaction is carried out in the presence of a base. Examples of bases for the reaction include inorganic bases (e.g., sodium hydroxide, potassium hydroxide, sodium carbonate, sodium hydrogen carbonate or sodium acetate) and organic bases (e.g., triethylamine, pyridine or DBU). Sodium carbonate and sodium hydrogen carbonate are particularly preferred. A suitable amount for the base is about 1 to 40 mols per mol of the four-equivalent coupler, preferably 1 to 5 mols per mol.

The reaction is carried out at −5° C. to 200° C., preferably 10° to 100° C. As the matter of fact, the reaction temperature, reaction solvent and reaction time depend on the products synthesized.

The thus-obtained compound of the formula (I) is washed with a solvent having strong extraction power (e.g., ether, ethyl acetate or chloroform) in a volume of 2 to 10 times the reaction system. Water-soluble ureas can be removed by washing. Then, a drying agent such as anhydrous sodium sulfate or anhydrous magnesium sulfate is added to the extracted liquid and then the mixture is concentrated to obtain the pure compound of the formula (I). If necessary, the compound can be recrystallized from a poor solvent to provide a purer compound.

According to the method of this invention, couplers having an alkylthio group can be prepared in high yield and improved purity. As is discussed above and as will later be demonstrated, the prior art methods do not provide alkylthiosubstituted couplers appreciably or in good yield and good purity. Couplers in which the coupling active position is unsubstituted are advantageously used as the starting material. Further, according to the method of this invention, the final products can be obtained in not less than 95% conversion rate. Since the products are prepared in high yield, it is unnecessary to use complicated operations such as column chromatography for separation and purification of the products, and pure compounds can be easily obtained simply by recrystallization.

Two-equivalent couplers prepared by the method of the invention are shown below.

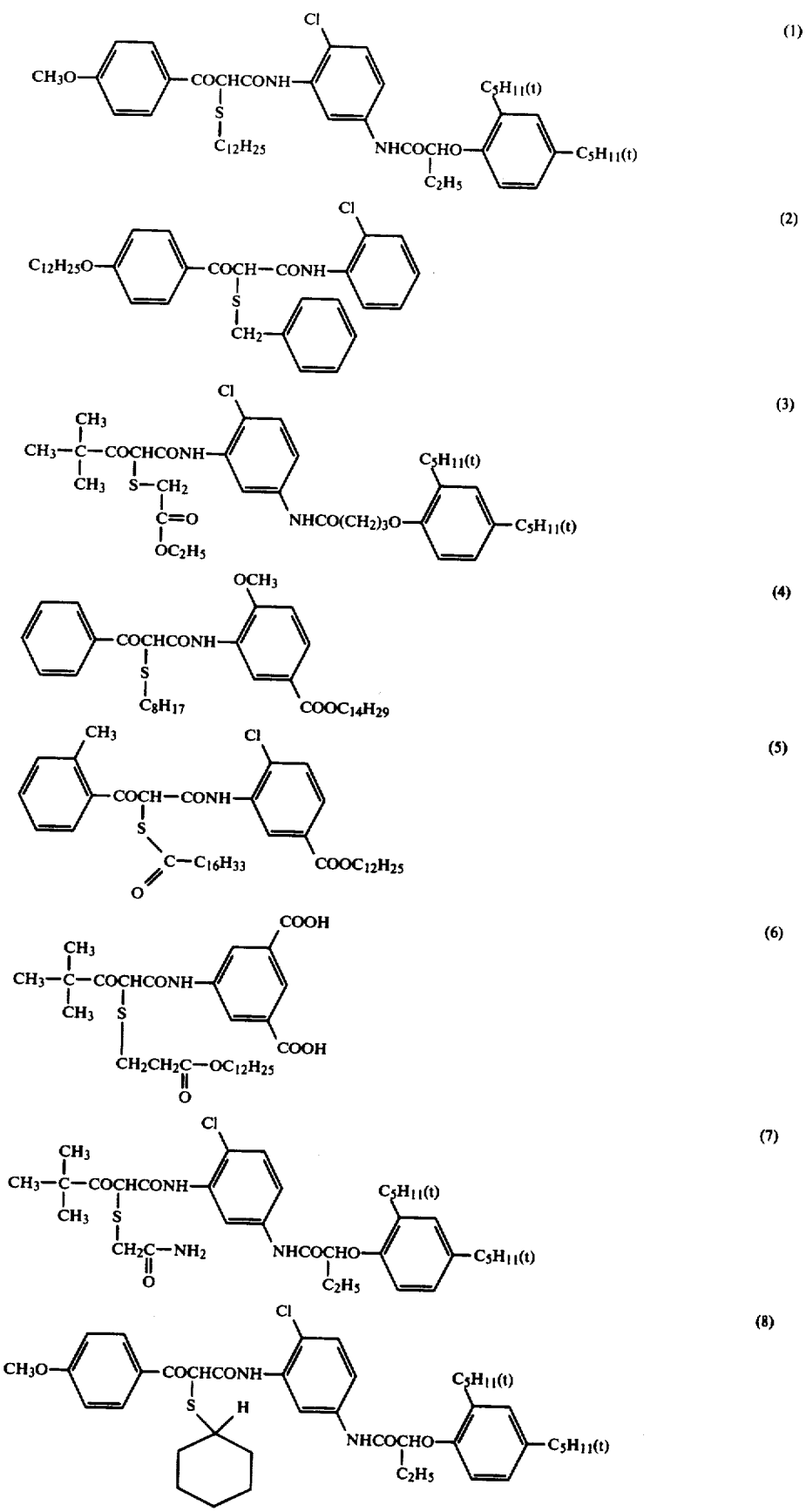

-continued
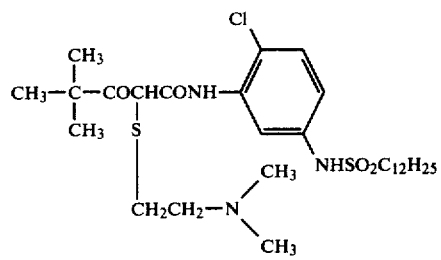 (9)
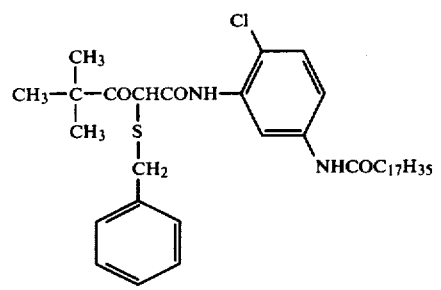 (10)
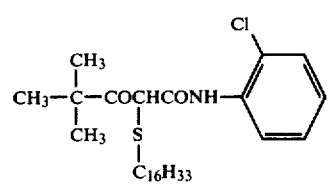 (11)
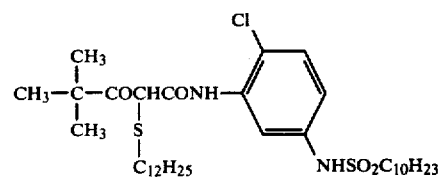 (12)
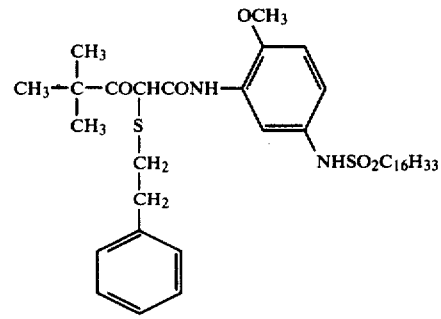 (13)
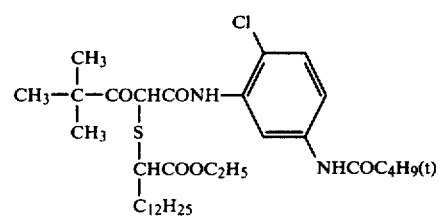 (14)
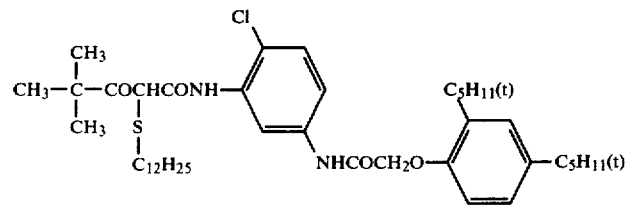 (15)

-continued
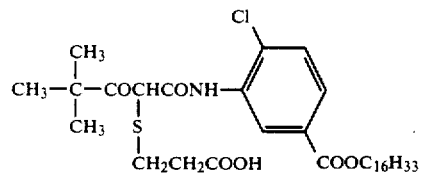 (16)
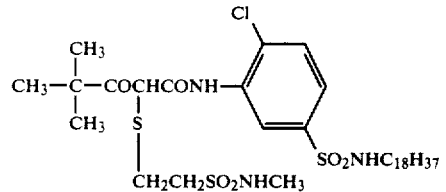 (17)
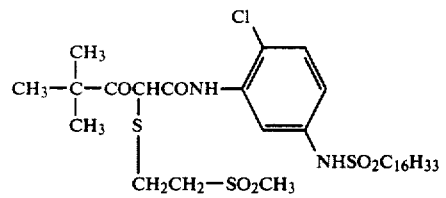 (18)
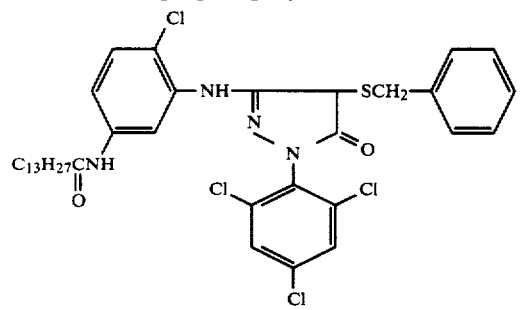 (19)
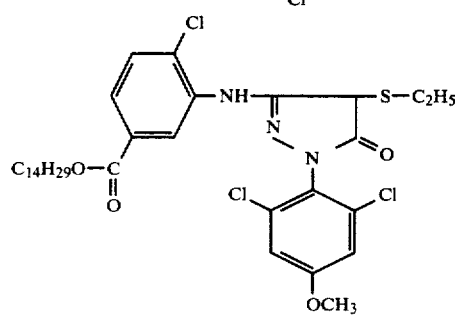 (20)
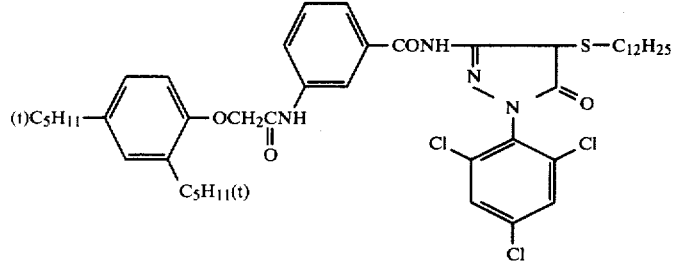 (21)
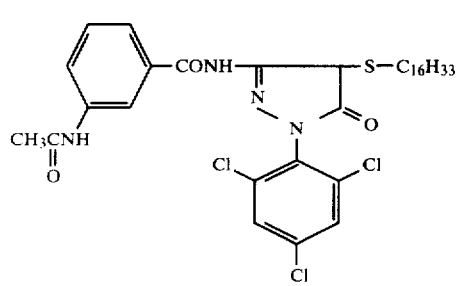 (22)

-continued
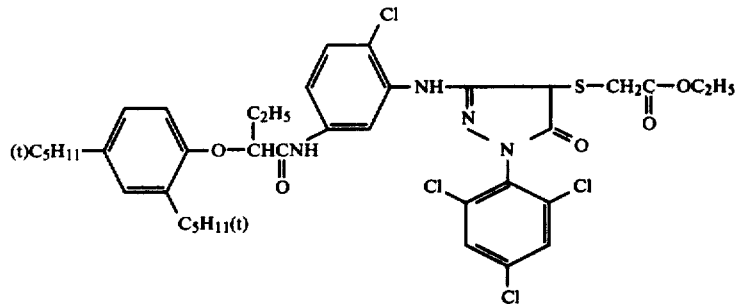 (23)
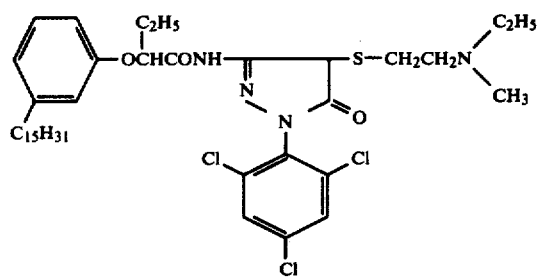 (24)
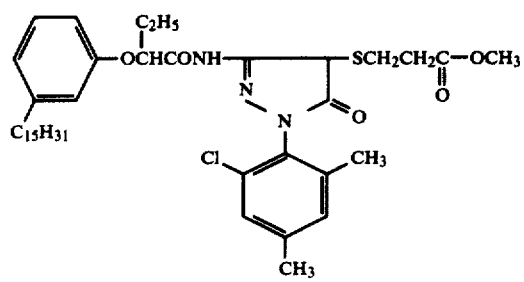 (25)
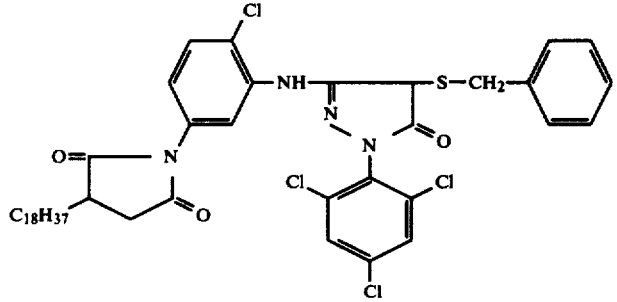 (26)
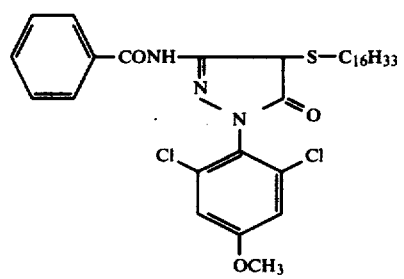 (27)
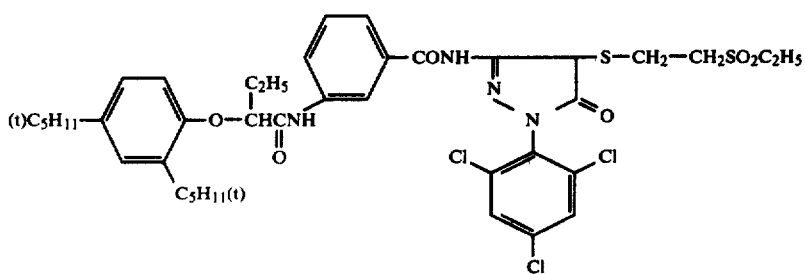 (28)

-continued
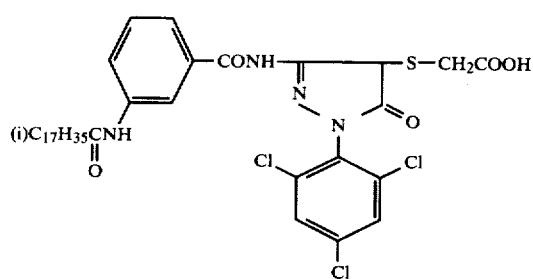 (29)
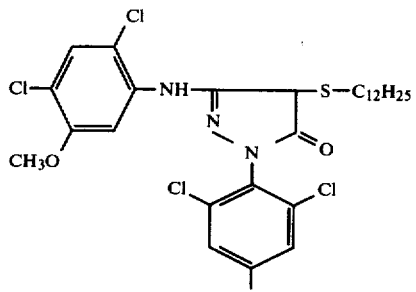 (30)
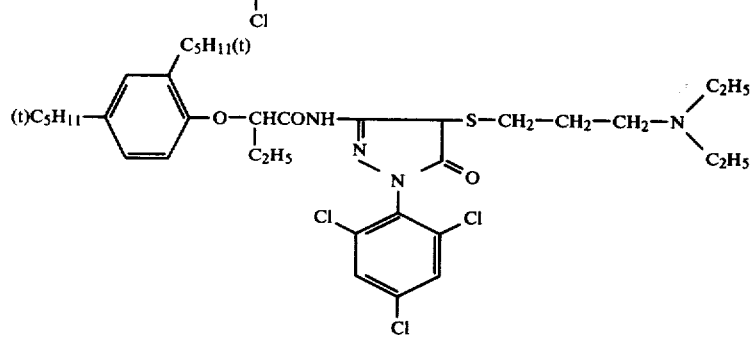 (31)
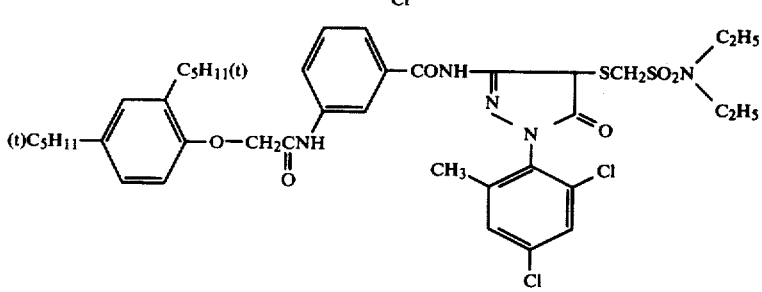 (32)
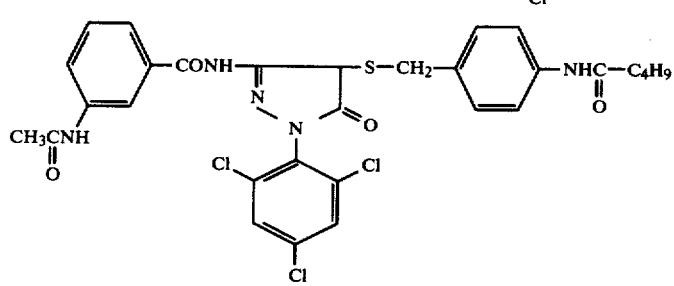 (33)
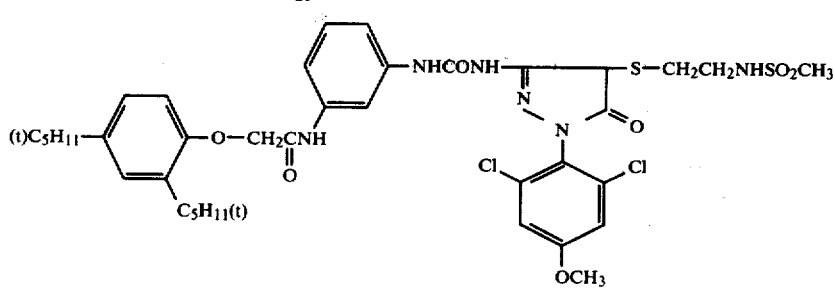 (34)

-continued
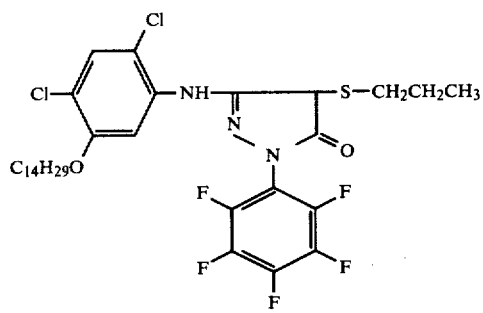 (35)
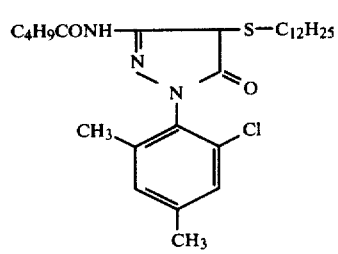 (36)
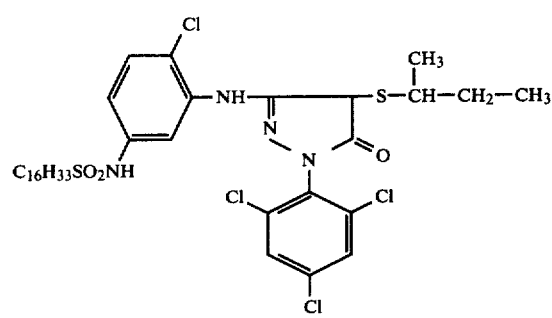 (37)
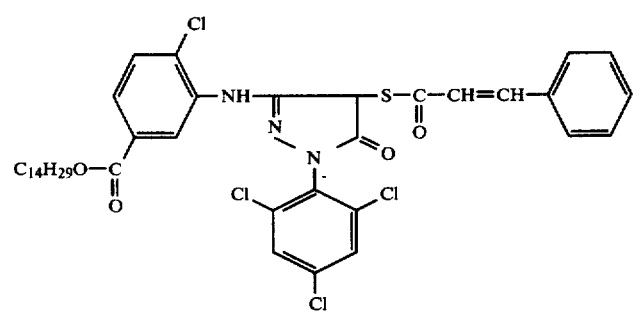 (38)
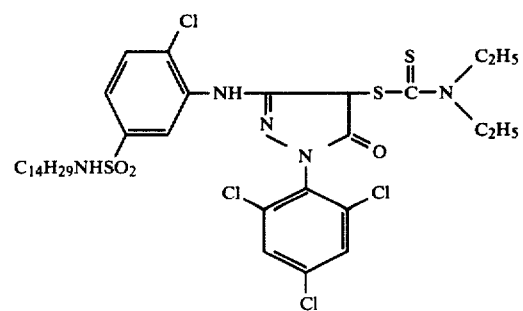 (39)

-continued
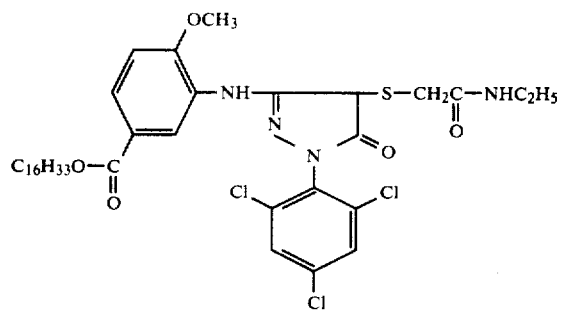
(40)
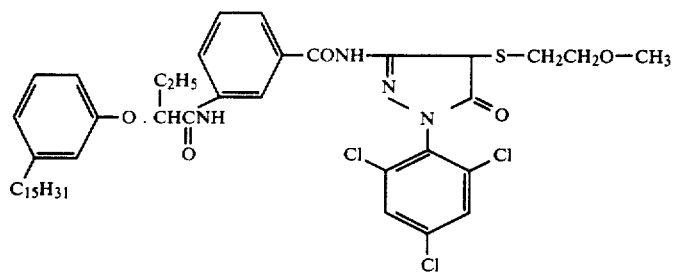
(41)
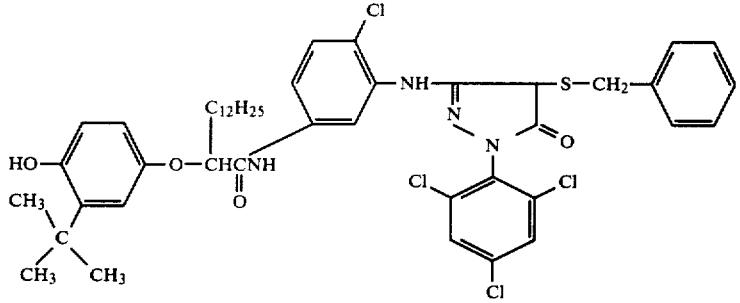
(42)
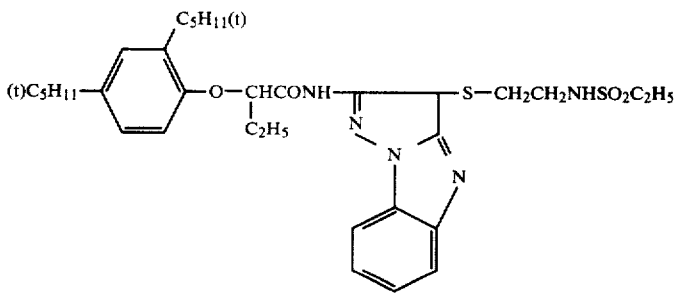
(43)
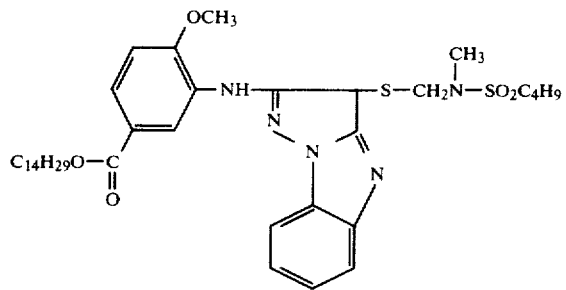
(44)
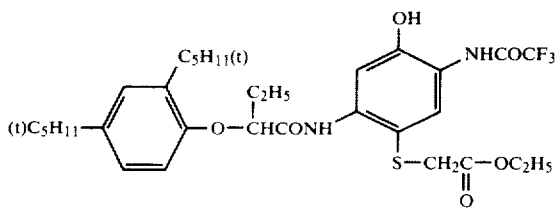
(45)

-continued
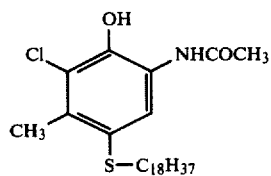
(46)
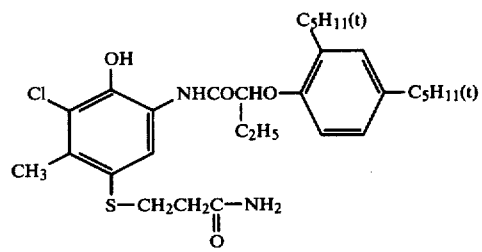
(47)
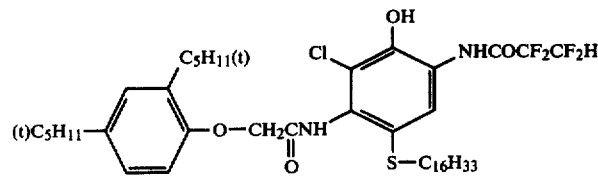
(48)
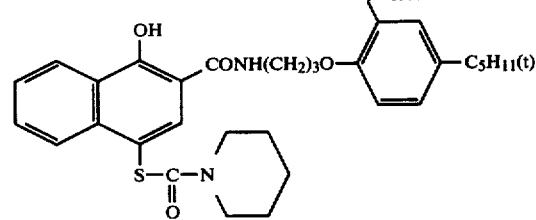
(49)
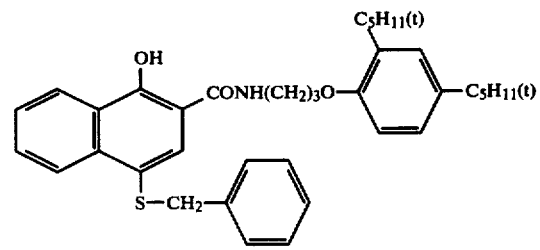
(50)
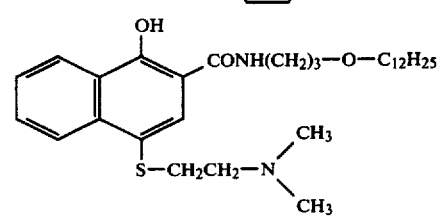
(51)
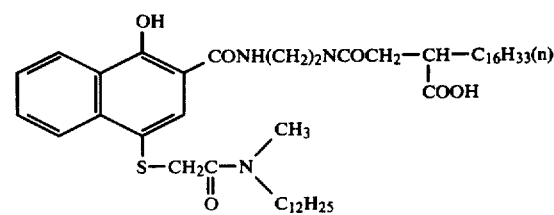
(52)
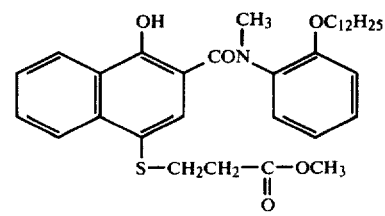
(53)

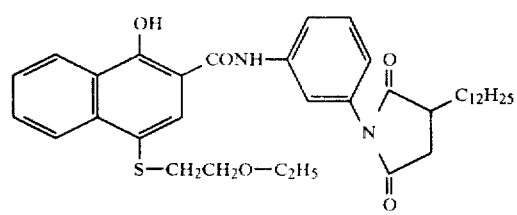
(54)
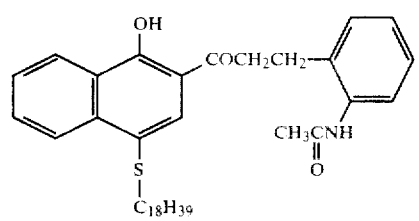
(55)
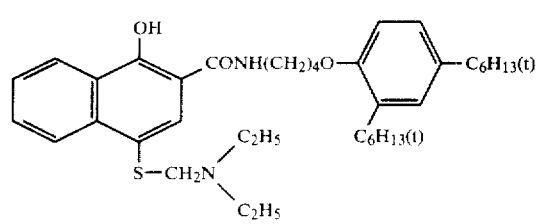
(56)
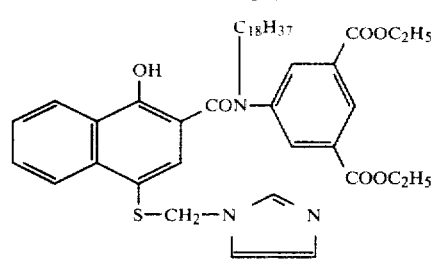
(57)
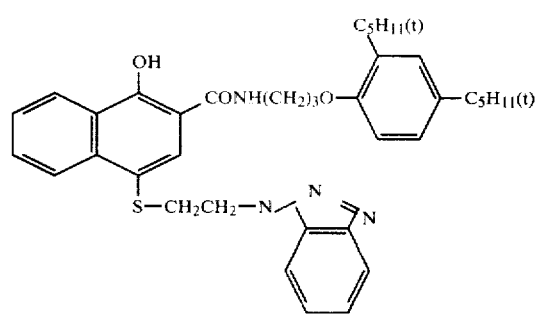
(58)
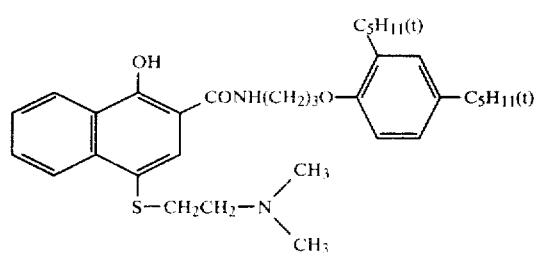
(59)
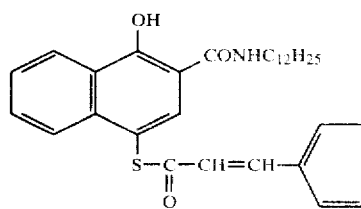
(60)

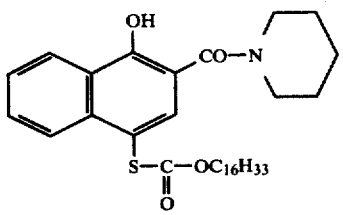 (61)

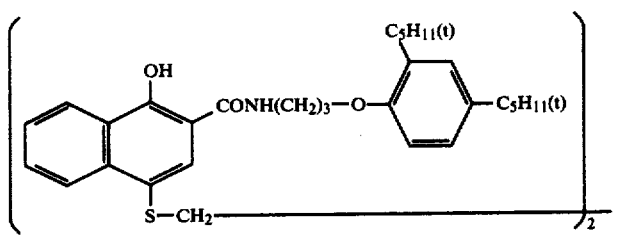 (62)

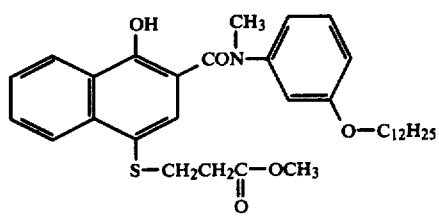 (63)

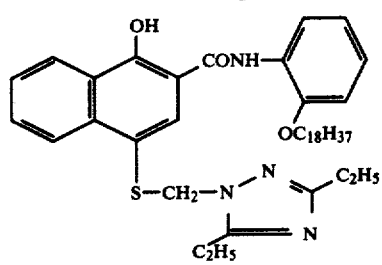 (64)

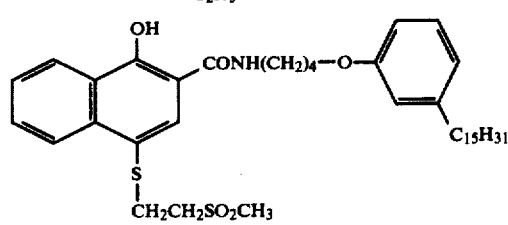 (65)

Synthetic examples of the typical couplers by the method of the present invention are shown below, but the method of this invention is not limited to these examples.

EXAMPLE 1

Preparation of 1-(2-chloro-4,6-dimethyl)phenyl-3-pentamido-4-dodecylthio-5-oxo-2-pyrazoline (Compound 36)

3.2 g of 1-(2-chloro-4,6-dimethyl)-3-pentadecanamido-5-pyrazolone was dissolved in 80 cc of 80% ethanol (volume ratio of ethanol to water: 4:1), 0.8 g of potassium carbonate was then added, 3.2 g of S-n-dodecylthioisothiourea hydrochloride dissolved in 30 cc of ethanol was dropwise added over a period of 5 minutes on a steam bath with stirring, and the mixture was stirred under heating for 10 minutes. After cooling with flowing water, 100 cc of ethyl acetate was added, the mixture was washed with water twice, and ethyl acetate layer was dried with anhydrous sodium sulfate (conversion rate: 95%). Sodium sulfate was removed and the sovlent was concentrated under reduced pressure to crystallize the residue from n-hexane. Thus obtained crystal was recrystallized from n-hexane to obtain 4.2 g of Compound 36 having a melting point of 47° to 48° C.

Elemental Analysis for $C_{28}H_{44}ClN_3O_2S$: Calcd.(%): H: 8.49; C: 64.40; N: 8.05. Found (%): H: 8.54; C: 64.24; N: 8.10.

EXAMPLE 2

Preparation of Compound 21

33.5 g of 1-(2,4,6-trichlorophenyl)-3-{3-[(2,4-di-t-amylphenoxy)acetamido]benzamido}-5-oxo-2-pyrazoline and 3.5 g of potassium carbonate were added to 200 ml of 80% aqueous ethanol (ethanol:water = 80:20 by volume). The mixture was heated with stirring on a steam bath. To the mixture, a solution of 18.7 g of S-n-dodecylthioisothiourea hydrochloride in 100 ml of ethanol was dropwise added. The resulting mixture was heated to reflux for 15 minutes and then poured into ice water. The mixture was neutralized with ethyl acetate and then washed with an aqueous acetic acid solution once and further with water twice. After drying over anhydrous sodium sulfate, the solvent was removed under reduced pressure. The residue was crystallized out from methanol to obtain 39 g of Compound 21 showing a melting point of 170° to 172° C. (conversion rate: 95%).

Elemental Analysis for $C_{46}H_{61}N_4O_4SCl_3$: Calcd.(%): C: 63.22; H: 7.05; N: 6.42. Found (%): C: 63.21; H: 7.01; N: 6.43.

COMPARATIVE EXAMPLE 1

13 g of 1-(2,4,6-trichlorophenyl)-3-{3-[(2,4-di-tert-amylphenoxy)butyramido]benzamido}-5-oxo-2-pyrazoline was added to 100 ml of 10% ethanol solution (volume ratio of water to ethanol: 1:9), 7.7 g of didodecyl disulfide prepared by oxidizing dodecylmercaptan with hydrogen peroxide, and 1.5 g of potassium carbonate were added, and then the resulting mixture was refluxed for 1 hour under heating. At this stage, no product was found on a thin layer chromatograph. Further, upon reflux under heating for 5 to 6 hours, reaction did not appreciably occur.

COMPARATIVE EXAMPLE 2

In accordance with the procedure disclosed in U.S. Pat. 3,227,554, an attempt to prepare Compound 21 was made.

13 g (0.063 mole) of dodecyl mercaptan was dissolved in 100 ml of carbon tetrachloride. The resulting solution was cooled to 5° to 10° C. Chlorine gas was bubbled into the solution, whereby heat generated and the temperature of the system elevated to 20° C. At this stage, the reaction liquid was changed to yellow and then the bubbling of chlorine ceased. Thereafter, nitrogen was introduced into the system to take the excess chlorine away.

A solution of 42 g (0.063 mol) of 1-(2,4,6-trichlorophenyl)-3-{3-[(2,4-di-t-amylphenoxy)acetamido]benzamido}-5-oxo-2-pyrazoline in 400 ml of chloroform was cooled to 15° to 20° C. The dodecyl mercaptan reaction liquid previously prepared as above was dropwise added to the solution. The mixture was allowed to stand overnight. Thereafter, the mixture was washed with water, neutralized with sodium bicarbonate and again washed with water. After drying over anhydrous sodium sulfate, the solvent was removed under reduced pressure. The oily residue was crystallized out with ethyl acetate to obtain 25 g of colorless crystals having a melting point of 205° to 207° C. The product was verified by NMR spectrum, mass spectrum and elemental analysis to be 1-(2,4,6-trichlorophenyl)-3-{3-[(2,4-di-t-amylphenoxy)acetamido]benzamido}-4,4-dichloro-5-oxo-2-pyrazoline. The desired Compound 21 could not be produced.

EXAMPLE 3

Preparation of 1-(2,4,6-trichlorophenyl)-3-(2,4-dichloro-5-methoxyanilino)-4-dodecylthio-5-oxo-2-pyrazoline (Compound 30)

15.1 g of 1-(2,4,6-trichlorophenyl)-3-(2,4-dichloro-5-methoxyanilino)-5-pyrazolone was dissolved in 500 cc of 80% ethanol (volume ratio of ethanol to water: 4:1), and 2.5 g of potassium carbonate was added. 10.4 g of S-(n-dodecylthio)isothiourea hydrochloride dissolved in 100 cc of ethanol was dropwise added over a period of 10 minutes on a steam bath with stirring under heating, and further, the mixture was stirred under heating. After cooling with flowing water, 300 cc of ethyl acetate was added, followed by washing twice with water. After drying ethyl acetate layer with anhydrous sodium sulfate, sodium sulfate was removed, the solvent was concentrated under reduced pressure, and the residue was crystallized from acetonitrile. The thus-obtained crystal was recrystallized from acetonitrile-ethyl acetate (volume ratio: 10:1) to obtain 18 g of the coupler having a melting point of 100° to 102° C. (conversion rate: 95%).

Elemental Analysis for $C_{28}H_{34}Cl_5N_3O_2S$: Calcd.(%): H: 5.24; C: 51.43; N: 6.43. Found (%): H: 5.25; C: 51.72; N: 6.38.

EXAMPLE 4

Preparation of 1-(2,4,6-trichlorophenyl)-3-(2-chloro-5-tetradecanamidoanilino)-4-benzylthio-5-oxo-2-pyrazoline (Compound 19)

21.4 g of 1-(2,4,6-trichlorophenyl)-3-(2-chloro-5-tetradecanamidoanilino)-5-oxo-2-pyrazoline was dissolved in 80% ethanol solution (volume ratio of water: 20%), 2.42 g of anhydrous potassium carbonate was added, and the mixture was refluxed under heating. To the solution, 8.2 g of S-benzylthioiosthiourea hydrochloride was added and stirred vigorously for 3 hours. After the completion of the reaction was confirmed on a thin layer chromatography, the reaction vessel was cooled. The thus-obtained crystal was filtered and was dissolved in 100 ml of heated ethanol. Undissolved substance was filtered and the filtered liquid was cooled to obtain the crystal which was colorless Compound 19 having a melting point of 182° to 185° C. with a yield of 12 g (conversion rate: 95%).

Elemental Analysis for $C_{36}H_{40}N_4O_2SCl_4$: Calcd.(%): H: 5.49; C: 58.56; N: 7.62. Found (%): H: 5.40; C: 58.49; N: 7.64.

While the invention has been described in detail and with reference to specific embodiments thereof, it will be apparent to one skilled in the art that various changes and modifications can be made therein without departing from the spirit and scope thereof.

What is claimed is:

1. A method for preparing a coupler represented by the formula (I):

A—S—R     (I)

which comprises reacting a disulfide compound represented by the formulae (IIa) or (IIb) with a compound of the formula A—H

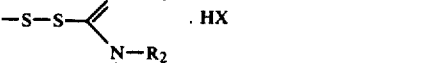

(IIa)

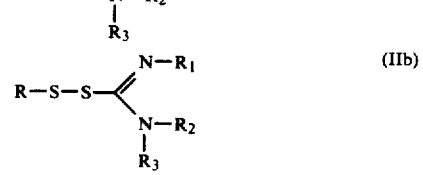

(IIb)

wherein A is a magenta coupler in which a hydrogen atom at the coupling active position is removed, wherein A is represented by the formula (IV):

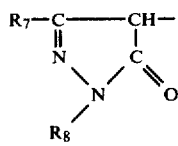

(IV)

wherein R₇ represents an anilino group, an acylamino group or a ureido group; and R₈ represents a group of the formula

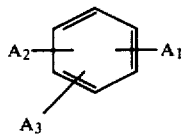

wherein $A_1$, $A_2$ and $A_3$, which may be the same or different, each represents a hydrogen atom, an alkyl group, a halogen atom, an alkoxy group, an aryloxy group, an acylamino group, a carbamoyl group, a sulfamoyl group, a sulfonyl group or a cyano group and wherein any R₇ or R₈ group of an aliphatic nature has 1-22 carbon atoms and any R₇ or R₈ group of an aromatic nature has 6-32 carbon atoms, R is a straight chain or branched chain alkyl group having 1 to 22 carbon atoms or a cyclic alkyl group having 5 to 22 carbon atoms, a cyclic alkenyl group having 6 to 22 carbon atoms, or an aralkyl group having up to

group, where B is —Y, —D—Y or

and D is an oxygen atom or

R₄ is a hydrogen atom, an alkyl group having 1 to 22 carbon atoms or an aryl group having 6 to 32 carbon atoms, Y is a straight chain or branched chain alkyl group having 1 to 22 carbon atoms or a cyclic alkyl group having 5 to 22 carbon atoms, a straight chain or branched chain alkenyl group having up to 22 carbon atoms or a cyclic alkenyl group having 5 to 22 carbon atoms, as aralkyl group having up to 32 carbon atoms, an aryl group having 6 to 32 carbon atoms, or a non-metallic heterocyclic group containing at least one carbon atom and comprising a 5 to 7-membered heterocyclic ring, Q is a non-metallic atom group necessary to complete a 5- or 6-membered nitrogen-containing heterocyclic ring containing at least one carbon atom, Z is an oxygen atom or a sulfur atom, $R_1$, $R_2$ and $R_3$ each is a hydrogen atom, an alkyl group having 1 to 22 carbon atoms, a cycloalkyl group having 5 to 22 carbon atoms or a substituted or unsubstituted phenyl group and $R_1$ and $R_3$ or $R_2$ and $R_3$ can combine to form a 5-, 6- or 7-membered nitrogen-containing heterocyclic ring containing at least one carbon atom and X is a halogen atom, said disulfide being reacted with said compound in the presence of a base and a solvent.

2. The method of claim 1, wherein said base is present in an amount of about 1 to 40 mols per mol of the compound A—H.

3. The method of claim 1, wherein said reaction is carried out at a temperature of about −5° C. to 200° C.

4. The method of claim 1, wherein the molar ratio of said disulfide represented by the formulae (IIa) or (IIb) to said compound of the formula A—H is 1:1 to 20:1.

5. The method of claim 1, wherein said acylamino group for R₇ is selected from the group consisting of acetylamino, and 3-[(2,4-di-tert-amylphenyoxy)acetamido]benzamido.

6. The method of claim 1, wherein said ureido group for R₇ is selected from the group consisting of ureido, N-arylureido and N-alkylureido.

7. The method of claim 1, wherein said anilino group for R₇ is selected from the group consisting of N-methylanilino, N-acetylanilino and 2-chloro-5-tetradecanamidoanilino.

8. The method of claim 1, wherein said base is present in an amount of about 1 to 40 mols per mol of the compound A—H, the reaction is carried out at a temperature of about −5° C. to 200 C. and wherein the molar ratio of said disulfide represented by the formula (IIa) or (IIb) to said compound of the formula A—H is 1:1 to 20:1.

9. The method of claim 8, wherein the heterocyclic group represented by Y is selected from the class consisting of pyridyl, quinolyl, pyrrolidyl, benzimidazolyl, tetrahydrofurfuryl, benzofuryl, thienyl, benzothienyl, benzoxazolyl and benzothiazolyl.

10. The method of claim 1, wherein the heterocyclic group completed by Q is selected from the group consisting of pyrrolidine, piperidine, morpholine, imidazole, benzimidazole, phthalimide, succinimide, glutarimide, hydantoin, oxazolidindion, benzotriazole, α-pyridone, γ-pyridone, oxazolidone, valerolactam, butyrolactam, thiohydantoin, naphthotriazole, tetrazole, pyrazole, indole, imidazoline, pyrazoline, piperazine, indoline and isoindoline.

11. The method of claim 10, wherein $R_1$ and $R_3$ or $R_2$ and $R_3$, when they combine to form said 5-, 6- or 7-membered nitrogen-containing heterocyclic ring yield a ring selected from the group consisting of imidazolyl, pyrrolyl, piperidyl and morpholyl.

* * * * *